United States Patent [19]
Rishton

[11] Patent Number: 5,634,893
[45] Date of Patent: Jun. 3, 1997

US005634893A

[54] AUTOTRANSFUSION APPARATUS

[75] Inventor: Michael L. Rishton, Reading, Mass.

[73] Assignee: Haemonetics Corporation, Braintree, Mass.

[21] Appl. No.: 427,451

[22] Filed: Apr. 24, 1995

[51] Int. Cl.[6] ................................................ A61M 37/00
[52] U.S. Cl. .................................. 604/4; 604/7; 604/319
[58] Field of Search ................................ 604/4, 5, 6, 7, 604/28, 35, 319

[56] References Cited

U.S. PATENT DOCUMENTS

| | | | |
|---|---|---|---|
| 4,016,077 | 4/1977 | Schreiber | 604/49 |
| 4,033,345 | 7/1977 | Sorenson et al. | |
| 4,116,845 | 9/1978 | Swank | 210/446 |
| 4,475,904 | 10/1984 | Wang | 604/119 |
| 4,569,674 | 2/1986 | Phillips et al. | |
| 4,626,248 | 12/1986 | Scheller | 604/319 |
| 4,655,754 | 4/1987 | Richmond et al. | |
| 4,705,497 | 11/1987 | Shitaokoshi et al. | |
| 4,744,785 | 5/1988 | Rosenthal et al. | |
| 4,773,897 | 9/1988 | Scheller et al. | 604/34 |
| 4,826,494 | 5/1989 | Richmond et al. | |
| 4,846,800 | 7/1989 | Ouriel et al. | 604/4 |
| 4,870,975 | 10/1989 | Cronk et al. | |
| 4,898,572 | 2/1990 | Surugue nee Lasnier | |
| 4,909,780 | 3/1990 | Ouriel et al. | |
| 4,994,022 | 2/1991 | Steffler et al. | |
| 5,024,613 | 6/1991 | Vasconcellos et al. | |
| 5,100,376 | 3/1992 | Blake, III | |
| 5,203,778 | 4/1993 | Boehringer et al. | |
| 5,270,005 | 12/1993 | Raible | |

*Primary Examiner*—John G. Weiss
*Assistant Examiner*—Francis K. Cuddihy
*Attorney, Agent, or Firm*—Cesari and McKenna

[57] ABSTRACT

An autotransfusion apparatus for collecting salvaged blood includes an upper chamber for collecting blood and a lower chamber for receiving blood from the upper chamber. The upper chamber is subjected to a vacuum to withdraw blood from a patient. Particles and lipids are removed from the collected blood by a particle filter and a lipid separator. A selector valve located between the vacuum port and the lower chamber, and between the lower chamber and a vent, selectively couples lower chamber either to the vacuum source or the vent. The lower chamber receives blood from the upper chamber through a pressure-operated drain valve only when the lower chamber is coupled to the vacuum source. Coupling the lower chamber to the vent while the upper chamber is subjected to the vacuum source causes a pressure differential between the chambers, closing the pressure-operated drain valve. This allows the upper chamber to remain under a vacuum and continuously collect blood while the lower chamber drains blood into a blood bag.

10 Claims, 12 Drawing Sheets

AUTOTRANSFUSION APPARATUS

FIELD OF THE INVENTION

This invention relates to medical equipment, and in particular to an autotransfusion apparatus for collecting blood and reintroducing it, with reduced lipids, into the patient.

BACKGROUND OF THE INVENTION

When a patient loses a significant amount of blood from a wound or operation site, that blood must be replaced. Due to the risk of blood-transmitted diseases, however, it is desirable to limit the amount of donated blood that is infused. This can be accomplished by collecting the blood lost by the patient, processing the blood with a recovery system to remove any bone chips, blood clots or lipids within the collected blood, and then reinfusing it back into the patient. Salvaging a patient's own blood limits the amount of donated blood the patient must receive, thereby reducing the risk of exposure to disease.

Blood-recovery systems typically suction blood from the wound or operation site through a suction hose leading to a collection reservoir, which is also connected to a vacuum source. The vacuum draws blood into the reservoir via the suction hose. Ordinarily, the path from the hose to the reservoir passes through one or more blood filters. Once the collection reservoir is full, the blood is drained into a collection bag for reinfusion or later use. Generally, in order to drain the blood from the reservoir, it is necessary to break the vacuum within the reservoir by, for example, venting the reservoir to the atmosphere. In many blood-recovery systems, this operation necessarily interrupts the flow of blood since a vacuum is necessary to draw blood into the reservoir.

Various attempts have been made to provide apparatus capable of collecting blood from a patient continuously. U.S. Pat. No. 5,024,613, for example, describes a device that can continuously collect blood from a patient while simultaneously draining the processed blood from the reservoir. The '613 device employs three chambers separated from each other by a series of valves. The middle chamber serves as a transition chamber between a lower-pressure collection chamber and a higher-pressure drainage chamber. This configuration permits isolation of the lower-pressure collection chamber from the higher-pressure drainage chamber, enabling the collection chamber to remain under a constant vacuum even as blood is drained from the drainage chamber. This type of device is complex and requires an extra chamber, thereby increasing its size.

Another apparatus for continuously collecting and reinfusing blood is described in U.S. Pat. No. 4,909,780. That device has a two-chambered reservoir and a rotatable manifold. The manifold can be positioned to allow one chamber to collect blood while the other chamber is reinfusing blood into the patient. This approach is also complex due to the number of parts required.

A simpler apparatus is described in U.S. Pat. No. 5,100,376. With this device, blood is collected under vacuum in a collection chamber that empties into a blood bag. When the weight of the blood collected in the collection chamber exceeds the pressure exerted by the vacuum in the collection chamber, blood drains into the lower bag. A problem with this design is that the vacuum in the collection chamber must be weak enough to allow blood to drain into the blood bag. If the vacuum in the collection chamber exceeds the weight of the blood contained in the collection chamber, no blood will drain into the blood bag.

SUMMARY OF THE INVENTION

The present invention provides a simple and compact apparatus for collecting and processing salvaged blood, and which facilitates simultaneous collection and drainage of blood without interrupting the incoming flow. The invention includes a first chamber for collecting blood. An inlet port on the first chamber admits blood into the chamber through a particle filter, which removes particles from the incoming blood. The first chamber includes a lipid separator, which separates undesirable lipids or other buoyant substances from the collected blood. A vacuum port on the first chamber couples the chamber to a vacuum source. The first chamber is connected to a second chamber into which collected blood drains; preferably, the second chamber is located below the first chamber so that blood can drain into the second chamber by gravity through a drain valve. A selector valve selectably couples the second chamber either to the vacuum source or to a vent. The drain valve closes when the second chamber is vented while the first chamber is coupled to the vacuum source, thereby isolating the chambers from one another and permitting the first chamber to remain under vacuum even as the vented second chamber drains into a blood bag.

In preferred embodiments, the drain valve is pressure-operated. The drain valve closes when subjected to a pressure differential between the first and second chambers (caused, for example, when the second chamber is vented while the first chamber is subjected to a vacuum).

In a preferred embodiment, the lipid remover comprises a partition within the first chamber that divides the chamber into two separate portions. The partition has an opening at its lower end that permits blood to pass thereunder while blocking the passage of buoyant material (such as lipids) floating on top of the blood. A dam spaced between the partition and the drain valve ensures that the lipid-containing surface of the blood remains above the partition opening; blood cannot flow into the drain valve until it reaches the height of the dam. In another preferred embodiment, the lipid separator is a lipid filter for filtering lipids from the blood.

BRIEF DESCRIPTION OF THE DRAWINGS

The foregoing and other objects, features and advantages of the invention will be apparent from the following detailed description of preferred embodiments, taken in conjunction with the following. The drawings are not necessarily to scale, emphasis instead being placed upon illustrating the principles of the invention.

DETAILED DESCRIPTION OF THE PREFERRED EMBODIMENTS

Figure 1:
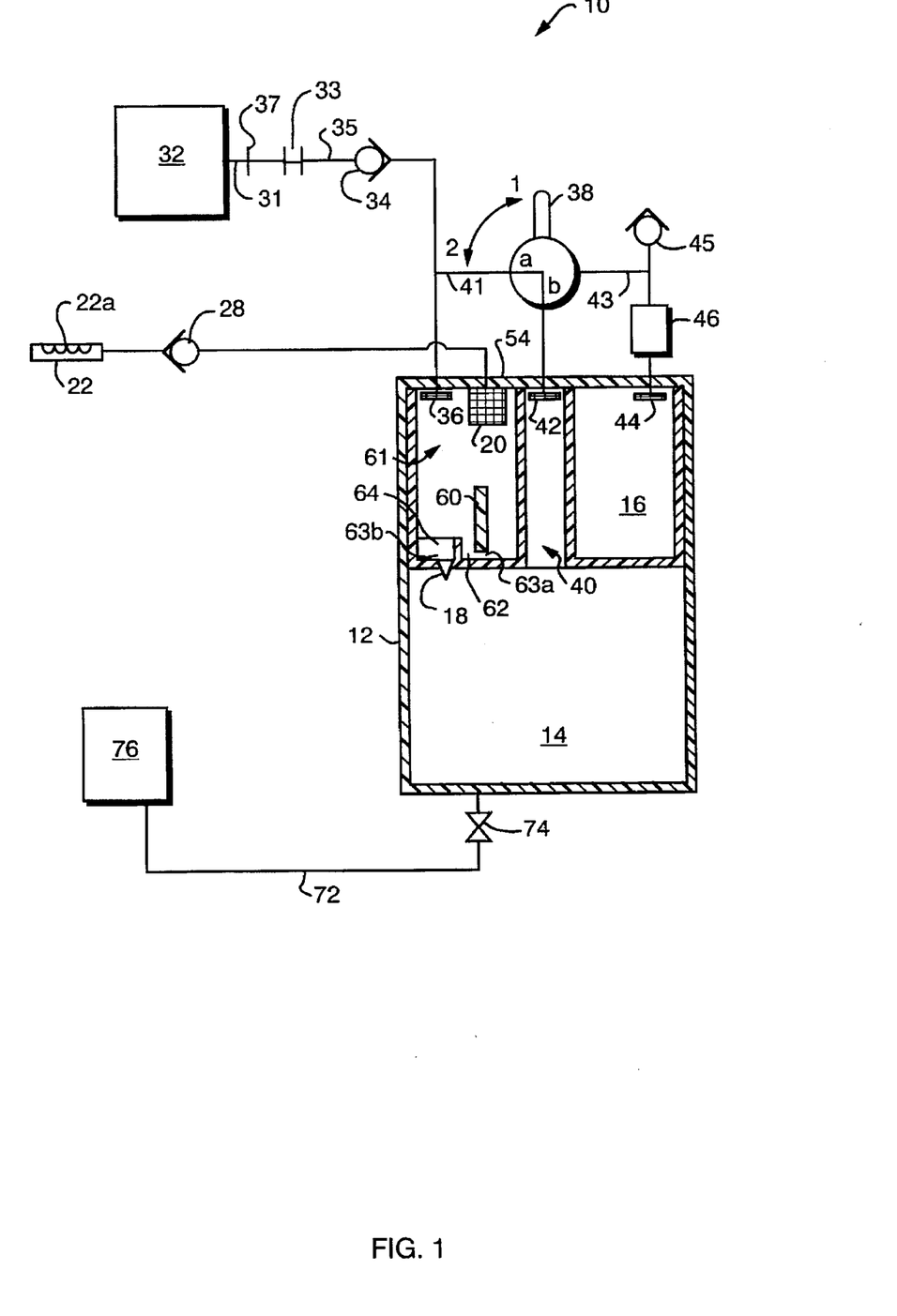
FIG. 1 is a schematic drawing of the present invention.

Refer first to FIG. 1, which illustrates an autotransfusion apparatus 10 in accordance with the present invention for collecting and processing blood from a wound or operation site. Apparatus 10 includes a generally cylindrical compound reservoir 12. A smaller, generally cylindrical housing forming an upper chamber 16 is disposed within the upper end of reservoir 12. The lower portion of reservoir 12 below upper chamber 16 forms a lower chamber 14. A blood bag 76 for collecting the processed blood is coupled to lower chamber 14 by a section of blood-compatible tubing 72 and a clamp 74 (which can, if desired, be replaced with a check valve). A flexible blood-compatible suction tube 22 for suctioning blood from a wound or operation site is coupled to upper chamber 16 by a check valve 28, a section of blood-compatible tubing 30, a blood inlet port 54 (which is preferably barbed) and a particle filter 20 (located in upper chamber 16).

Figure 2:
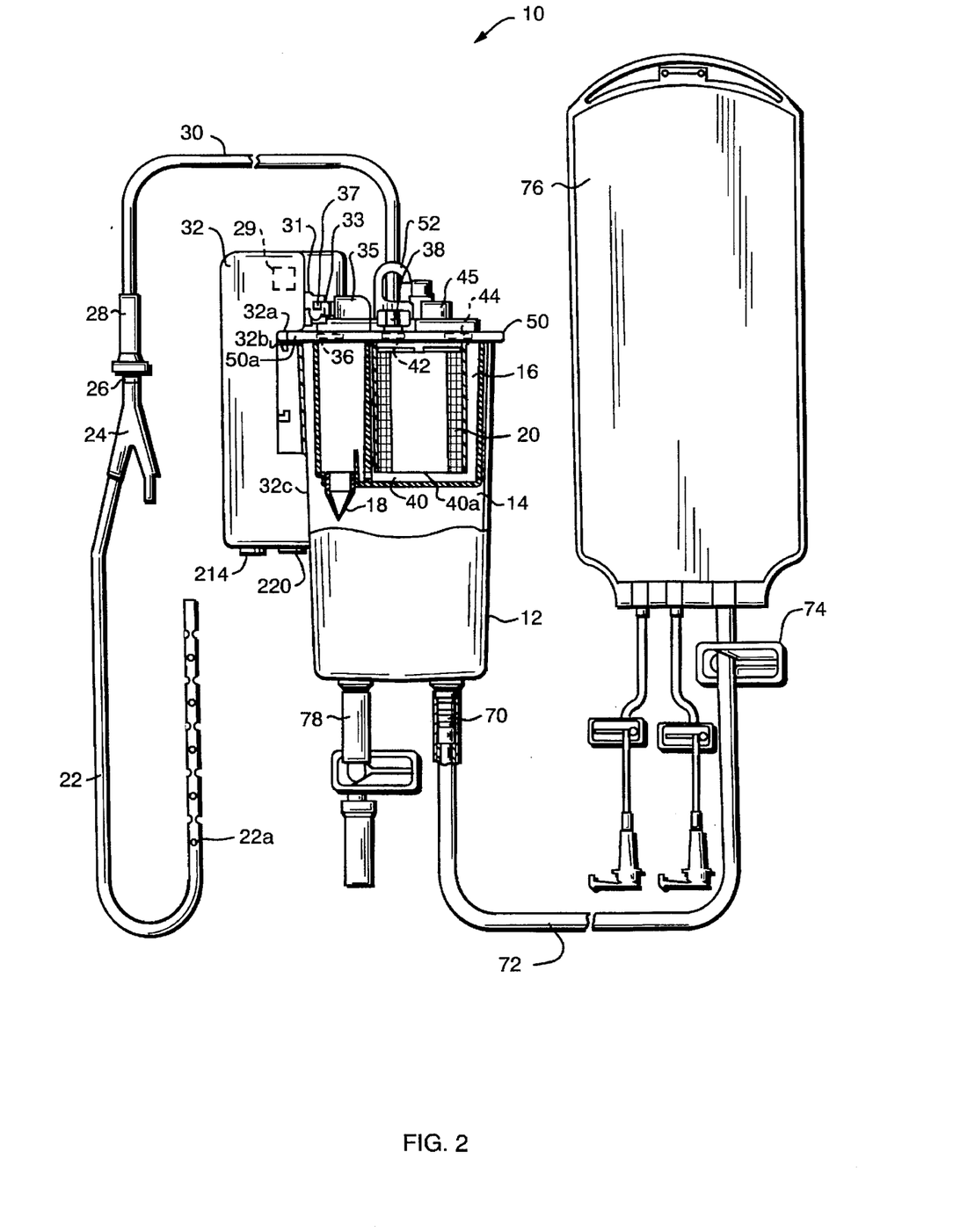
FIG. 2 is a side view of the invention showing the reservoir in section.

As best illustrated in FIG. 2, a vacuum source 32 for creating a vacuum in upper chamber 16 is coupled to upper chamber 16 via a female connector 31, a male connector 33, vacuum port 35, O-ring 37, a check valve 34 (see FIG. 1.) and a vacuum hydrophobic filter 36 (located in upper chamber 16). Vacuum source 32 is also in selective communication with lower chamber 14 via passage 41 (see FIG. 3), a selector valve 38, and a vent hydrophobic filter 42 (located in a passage 40 leading to lower chamber 14 along the side of the upper chamber 16). Lower chamber 14 is in selective communication with the atmosphere via passage 40, vent hydrophobic filter 42, selector valve 38, passage 43 and vent 45.

Selector valve 38 defines a closed fluid path between two ports a and b, (see FIG. 1.) and is capable of coupling lower chamber 14 either to vacuum source 32 (along path 41) in a first position or to vent 45 (along path 43) in a second position. Upper chamber 16 remains coupled to vacuum source 32 regardless of the position of selector valve 38. A pressure-relief valve 46 connects upper chamber 16 to vent 45, via a hydrophobic filter 44, if the pressure within upper chamber 16 rises to a predetermined level. Hydrophobic filters 36, 42 and 44 allow the passage of air but not the passage of liquids and bacteria to and from upper chamber 16 and lower chamber 14.

A lipid-separation system 61 is located within upper chamber 16 for separating lipids and other buoyant substances from blood collected within upper chamber 16. The lipid-separation system 61 includes a semi-circular partition 60 having an opening 60a (see FIG. 6) at the bottom thereof. Partition 60 is separated from a semi-circular dam portion 64 by an intermediate moat 62 (see FIG. 5). Dam 64 surrounds a vacuum-operated duckbill drain valve 18 (or equivalent check valve, preferably allowing for high flow rates) located in the bottom of upper chamber 16, through which blood drains into lower chamber 14.

In operation, vacuum source 32 creates a vacuum within upper chamber 16 and lower chamber 14 via female connector 31, male connector 33, O-ring 37 and vacuum port 35 with selector valve 38 in the first position (such that ports a and b couple passage 41 to passage 40). Check valve 34 (within vacuum port 35) ensures that air cannot flow into reservoir 12 through connectors 31, 33. The vacuum created in upper chamber 16 suctions blood from a patient's wound through suction tube 22 and into upper chamber 16 via suction holes 22a, check valve 28, tubing 30, blood inlet port 54 and particle filter 20. Check valve 28 prevents any backflow of blood back into the patient's wound should the pressure in the wound fall below the pressure in upper chamber 16. Filter 20 filters blood clots or particles such as bone chips from the blood entering upper chamber 16.

Blood collecting within upper chamber 16 (see FIG. 6) flows under partition 60, through opening 60a and into moat 62. As the blood flows through opening 60a, partition 60 prevents any lipids floating on top of the blood from passing through opening 60a. When the blood within moat 62 rises to the height of dam 64, the blood flows over dam 64 (as shown by arrow 63b) and into lower chamber 14 via drain valve 18.

When a sufficient amount of blood has been collected in the lower chamber 14, selector valve 38 is rotated into the second position such that ports a and b are coupled to passages 43 and 40, respectively. This connects lower chamber 14 to the atmosphere via passage 40, selector valve 38, passage 43, vent 45, and hydrophobic filter 42 while upper chamber 16 remains connected to vacuum source 32. Venting lower chamber 14 to the atmosphere increases the pressure in that chamber while upper chamber 16 remains subjected to a vacuum by vacuum source 32. The pressure differential between lower chamber 14 and upper chamber 16 causes drain valve 18 to close. Upper chamber 16 therefore remains under a vacuum and continues to collect blood through suction tube 22.

With the pressure in lower chamber 14 at atmospheric, blood contained in lower chamber 14 drains freely from lower chamber 14 into blood bag 76 via tubing 72 with clamp 74 open. When lower chamber 14 is emptied of the brood, slide clamp 74 is closed and selector valve 38 rotated back to the first position, coupling ports a and b to passages 41 and 40, respectively, thereby reconnecting lower chamber 14 to vacuum source 32 and subjecting lower chamber 14 to a vacuum. This removes the pressure differential between upper chamber 16 and lower chamber 14, allowing drain valve 18 to open and blood collected in upper chamber 16 to again flow into lower chamber 14. In the event that pressure within upper chamber 16 rises excessively, pressure-relief valve 46 opens to the atmosphere.

If the patient is to be moved to another location, vacuum source 32 can be disconnected from reservoir 12 by disengaging male connector 33 from female connector 31. This allows the reservoir 12 to be moved with the patient but without moving the vacuum source 32. Check valve 34 closes upon separation of vacuum source 32 from reservoir 12 and maintains the vacuum within reservoir 12. As a result, blood can continue to be suctioned from the wound of the patient even after vacuum source 32 is disconnected from reservoir 12.

The blood collected within blood bag 76 can then be reinfused back into the patient or stored for later use.

Figure 3:
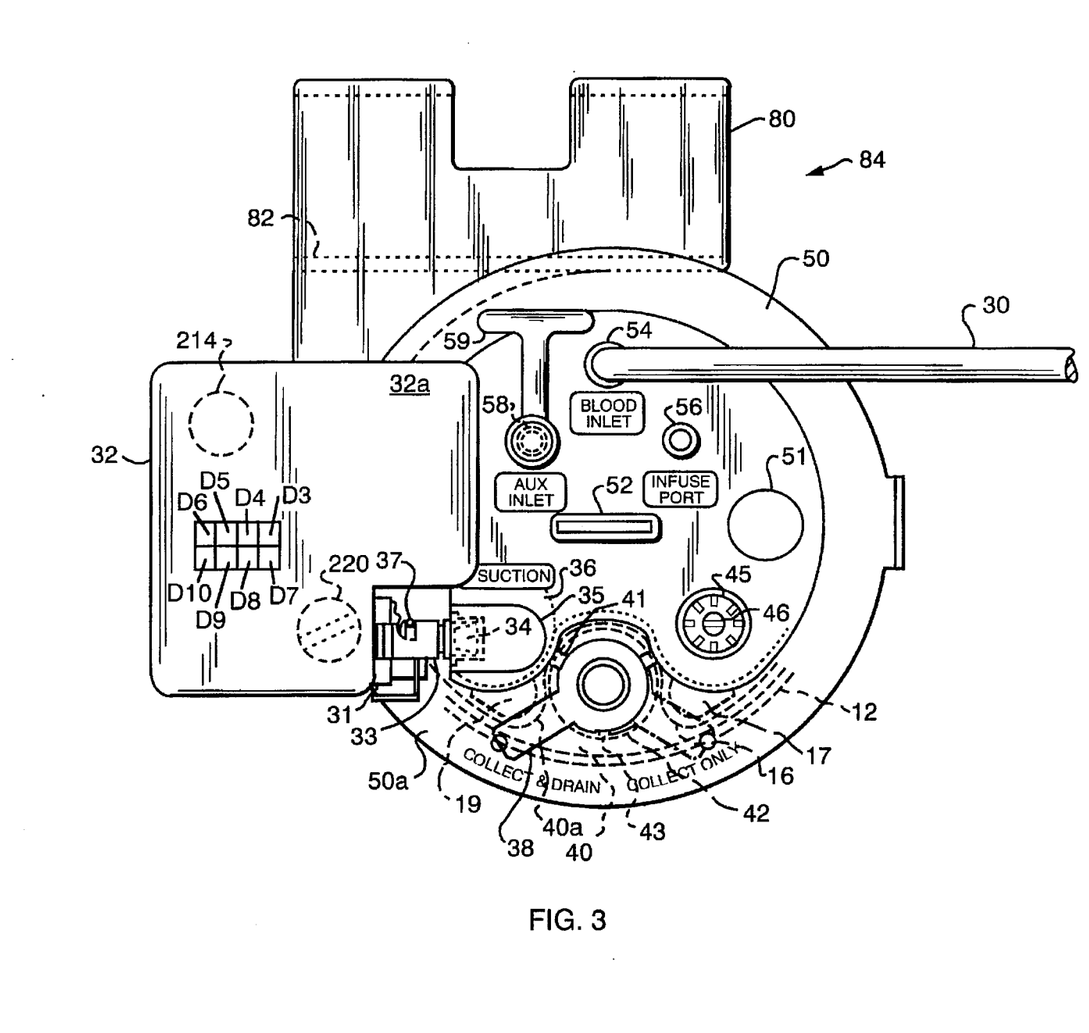
FIG. 3 is a top view of the invention.

With reference to FIGS. 2 and 3, suction tube 22 is coupled to check valve 28 by a connector 24 and tubing 26. Tubing 30 is coupled to blood inlet port 54 located on the top of apparatus 10 (see FIG. 3). Tubing 72 is coupled to the bottom of reservoir 12 by a connector 70. Additionally, a drain port 78 can be located beside connector 70 to direct blood contained within lower chamber 14 to another apparatus for further processing such as cell washing or cell separation.

Upper chamber 16 is an independent reservoir which fits within the top of reservoir 12 and descends from a top cap 50 that covers reservoir 12. An indented vertical recess 40a (see FIG. 5) on the outer surface of upper chamber 16 forms the passage 40 between the outer wall of upper chamber 16 and the inner surface of reservoir 12 to couple lower chamber 14 to vacuum source 32 or vent 45 via selector valve 38. Reservoir 12 and upper chamber 16 are preferably formed from molded biocompatible plastic. However, other suitable materials, such as stainless steel, can instead be employed. Drain valve 18 is preferably fabricated from a flexible and elastomeric material such as silicone or rubber, which allows it to collapse or close upon itself and close when the pressure in lower chamber 14 exceeds the pressure in upper chamber 16. Particle filter 20 is preferably a tubular mesh filter element supported by a tubular frame.

Vacuum port 35, selector valve 38 and vent 45 are located proximate to each other on top cap 50 at the top of reservoir 12, as best seen in FIG. 3. Preferably, top cap 50 includes an infusion port 56 and auxiliary port 58. Infusion port 56 permits drugs or anticoagulant to be added to incoming blood, while auxiliary port 58 (which is preferably barbed) provides an extra inlet for admitting any type of fluid into upper chamber 16. It is also possible to include a vacuum indicator 51 on top cap 50; in one embodiment, indicator 51 consists of a flexible dome extending outwardly which collapses inwardly to indicate a vacuum within upper chamber 16. In addition, a tear-away port cap 59 provides a leak-proof, sterile barrier for auxiliary port 58 and blood inlet port 54 prior to usage of these respective ports. A hook or handle 52 is centrally located on top cap 50 for carrying reservoir 12 to be conveniently carried. Hook 52 also allows reservoir 12 to be hung on an IV pole or to be otherwise suspended when a patient is being moved.

Vacuum source 32 is supported by reservoir 12 and is coupled to reservoir 12 by female connector 31, male connector 33 and O-ring 37, which securely engage each other to lock vacuum source 32 to reservoir 12. Female connector 31 is attached to vacuum source 32 while male connector 33 is mounted within vacuum port 35. Male and female connectors 33 and 31 are preferably commercially available "quick-disconnect" connectors. Male connector 33 has an elongate stem with an O-ring seal positioned about the stem in a groove. The female connector has a bore for accepting the stem of the male connector and a spring-loaded clip for locking the stem within the bore. The locking feature of connectors 31 and 33 secures vacuum source 32 to reservoir 12.

The lip 50a of top cap 50 is captured between a flange 32b and the upper portion 32a of vacuum source 32 (see FIG. 2). This arrangement helps prevent movement of vacuum source 32 relative to reservoir 12. The upper portion 32a of vacuum source 32 rests on top of reservoir 12 for support.

Figure 4:
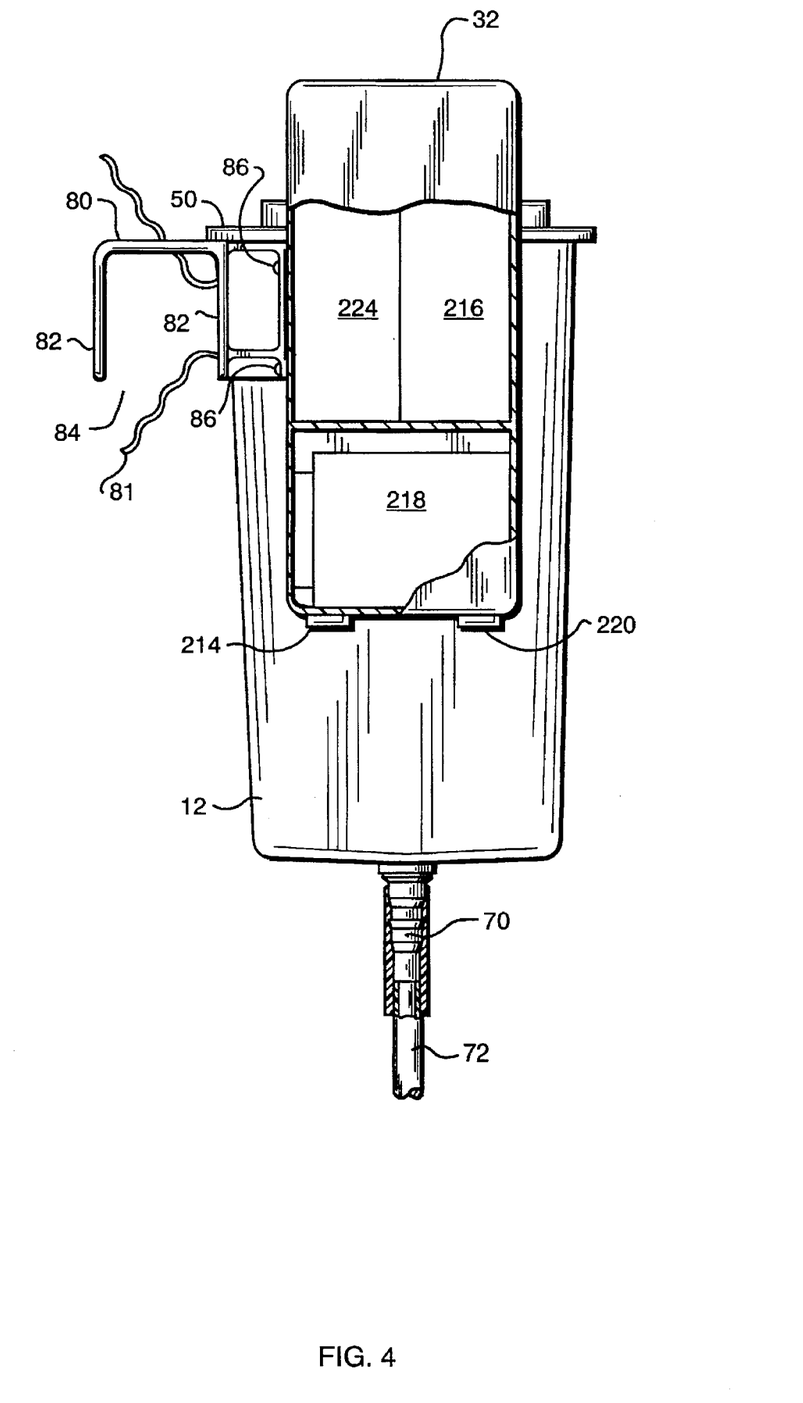
FIG. 4 is a rear view of the invention with a portion of the vacuum source housing broken away to show internal components.

Extending from the bottom of vacuum source 32 is a curved flange 32c, which contacts the side of reservoir 12 to provide the proper spacing between vacuum source 32 and reservoir 12. Flange 32 includes a normally open switch 29, which closes when reservoir 12 contacts flange 32c. Switch 29 allows power to be provided to vacuum source 32 only when reservoir 12 is secured to vacuum source 32, preventing vacuum source 32 from operating in the absence of a connection. Alternatively, switch 29 can be omitted. A hanging bracket 80 is secured to the side of vacuum source 32 by a set of screws 86 (see FIGS. 3 and 4). A dove-tail slide-like arrangement may also be employed to attach hanging bracket 80 to the vacuum source. Bracket 80 has two parallel members 82 extending downwardly from a horizontal plate to form a channel 84 therebetween. The channel 84 in bracket 80 allows vacuum source 32 and reservoir 12 to be hung from a horizontal bar such as a bed rail. An attachment strap 81 provides snug fastening when necessary.

Figure 5:
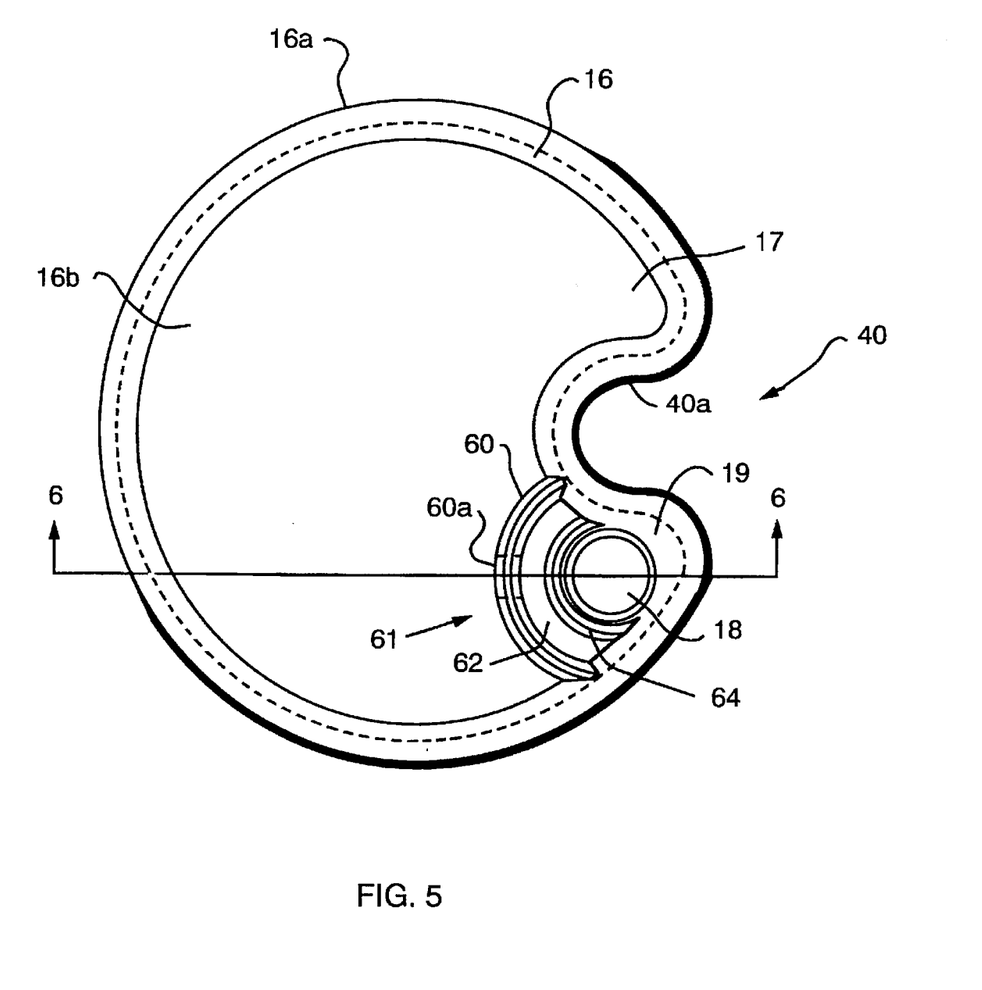
FIG. 5 is a top view of the upper chamber.
Figure 6:
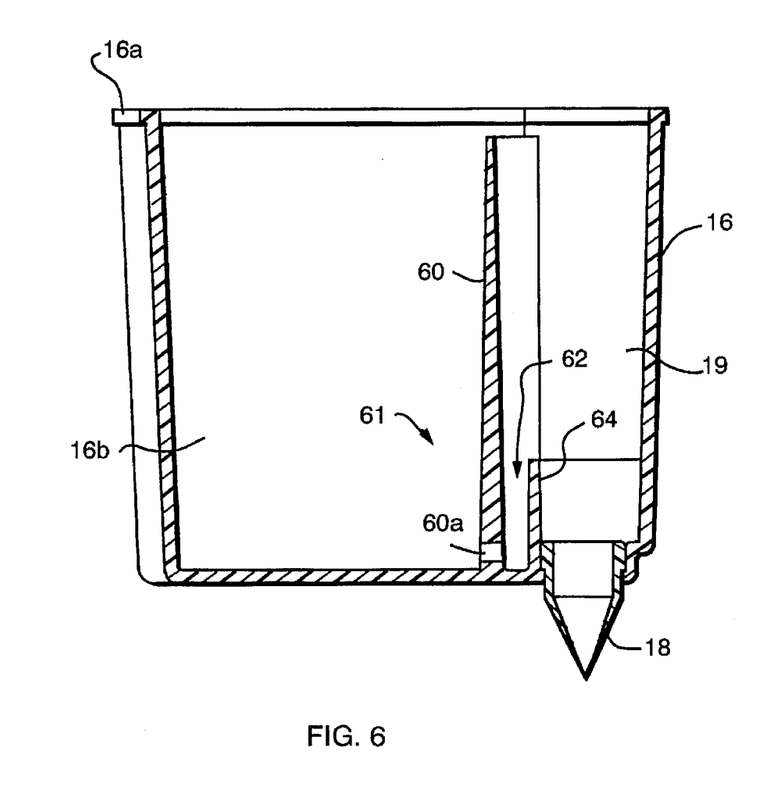
FIG. 6 is a sectional view of the upper chamber taken along lines 6—6 in FIG. 5.

With reference to FIGS. 5 and 6, upper chamber 16 includes a lip 16a which is dimensioned to be the same diameter as reservoir 12. This allows upper chamber 16 to rest on the top of outer reservoir 12 by means of lip 16a. On either side of vertical recess 40a are two coves 17, 19. Drain valve 18 and lipidseparating system 61 are located within cove 19. Dam 64 extends across cove 19 to enclose drain valve 18 within cove 19. Partition 60 is separated from dam 64 by moat 62 and also extends across cove 19 to isolate moat 62, dam 64 and valve 18 from the central portion 16b of upper chamber 16. Partition 60 extends upwardly from the bottom of upper chamber 16 almost to lip 16a.

Figure 7:
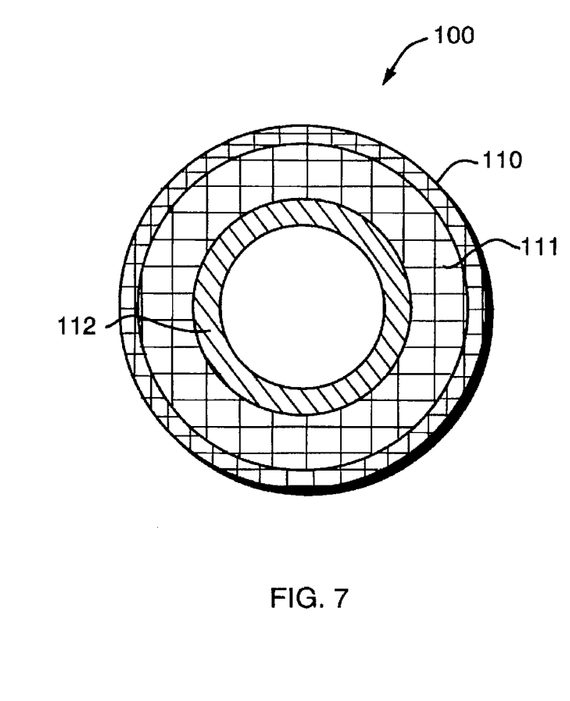
FIG. 7 is a cross-sectional view of a preferred filter.

FIG. 7 illustrates a form of filter that may be used in place of the simple particle filter 20 mentioned above and lipid-separation system 61. The depicted filter 100 removes particles, blood clots and lipids from incoming blood. A gross particle filter 111 can be added to minimize clogging of the outer filter 110. Filter 100 has an inner filter 112 made of lipophilic material for filtering lipids and an outer filter 110 for filtering particles. When filter 100 is used, partition 60 and dam 64 are no longer necessary since filter 100 removes the lipids.

Figure 8:
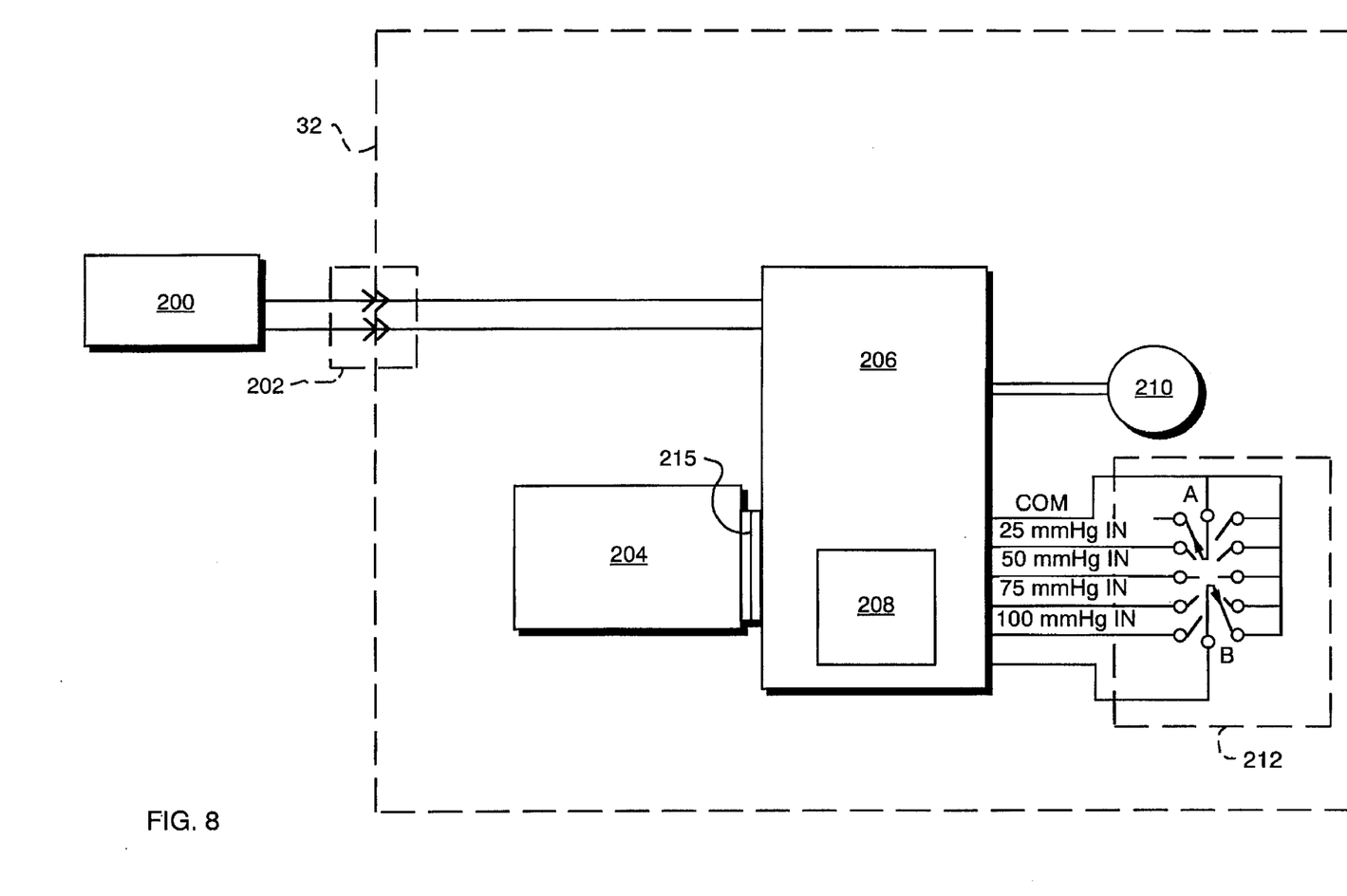
FIG. 8 is a schematic drawing of a preferred electrical control system for the present invention.

Refer not to FIG. 8, which shows the various operative components of the vacuum source 32. Generally, vacuum source 32 comprises a vacuum pump 224 in fluid communication with the reservoir 12 as described hereinabove. Vacuum pump 224 is driven by control circuitry contained on a circuit board 216. More specifically, an operator powers the vacuum source 32 and selects a desired level of vacuum by the operation of a power and vacuum control selector switch 220. Preferably, any of four vacuum levels, 100, 75, 50, and 25 mmHg, in addition to an off position, are selectable by this switch 220. The control circuitry detects the actual level of vacuum in the reservoir 12 by means of a vacuum sensor 230, which has a pressure transducer element in communication with the reservoir 12. On the basis of a comparison between the output from the vacuum sensor 230 and the position of the vacuum selector switch 220, the control circuitry drives vacuum pump 224 so that the level of vacuum in the reservoir 12 approaches that selected by the user.

Vacuum source 32 is electrically powered by one of two different sources. A rechargeable battery 204 is provided within the vacuum source 32 to power both the control circuitry and also vacuum pump 210. Electrical power can alternatively be supplied by an external AC/DC power supply 200 through a plug connector 202 positioned on the bottom of the vacuum source 32. The control circuitry uses the electrical power provided by power supply 200 both to operate the vacuum pump 210 and also to recharge the battery 204. The control circuitry can be divided into two sections, a charger/regulator circuit that controls the battery 204 charging voltage and control logic circuit that controls operation of the vacuum pump 210. A series of light emitting diodes (LEDs) indicate various parameters relating to the operating status of vacuum source 32, such as the vacuum level, whether the battery level is low, whether the battery is charging, the presence of an air leak, or if there is no flow.

Figure 9:
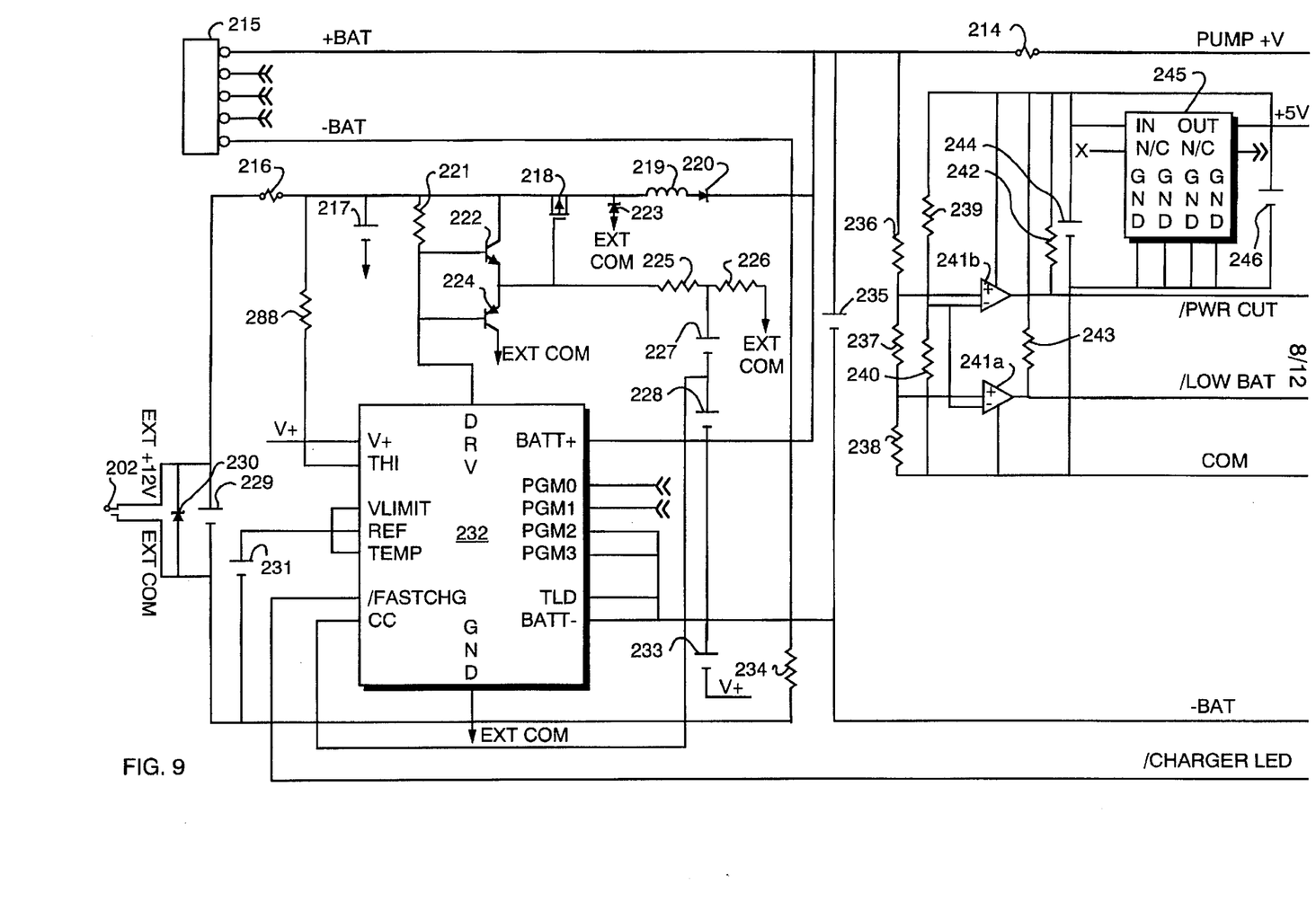
FIG. 9 is a schematic drawing of the charger/regulator circuit.

The charger/regulator circuit shown in FIG. 9 receives power from connector 202 when the vacuum source 32 is connected to external DC power source via lines EXT+12 V and EXT COM. A battery charger controller 232 monitors the voltage output of the rechargeable battery 204. After the charger controller 232 detects the active presence of external power supply 212, transistor T1 is turned on so that the rechargeable battery 204 can be recharged and the vacuum source 32 powered. A fuse 216 is placed in-line between the charger controller 232 and the external power supply 200 to protect vacuum source 32 during power surges. Detection of the active presence of external power supply 200 by charge controller 232 also causes the generation of a charge indication signal on a Charger LED 262.

The output voltage from voltage regulator 245 is also used as a voltage reference by two analog differential comparators 241a, 241b, which generate the low-battery and power-cut signals. Vacuum pump 210 will continue to operate as the available voltage drops, albeit with less efficiency. It is critical, however, that the regulated 5 V supplied by the voltage regulator 245 be maintained at all times. The power-cut comparator 241b, which generates a power cut signal (/PWR_CUT), protects against malfunctions that could occur should the operating voltage to fall below this level.

Specifically, low battery comparator 241a generates the low-battery signal (/LOW BAT) when the voltage on line Pump+V falls below 7.2 V. This function is achieved by a differential analog comparator 241a that receives a reference voltage via a set of resistors 238 and 236+237 from the +BAT line and a reference voltage which is divided by a pair of resistors 239, 240 connected between the output (+5 V) of the voltage regulator 245 and ground (COM). The power cut-off comparator 241b is similarly a differential analog comparator 241a except that resistors 237+238 and 236 have been selected so that it will generate the power cut signal (/PWR_CUT) when line PUMP+V drops below 6.0 V.

Figure 10:
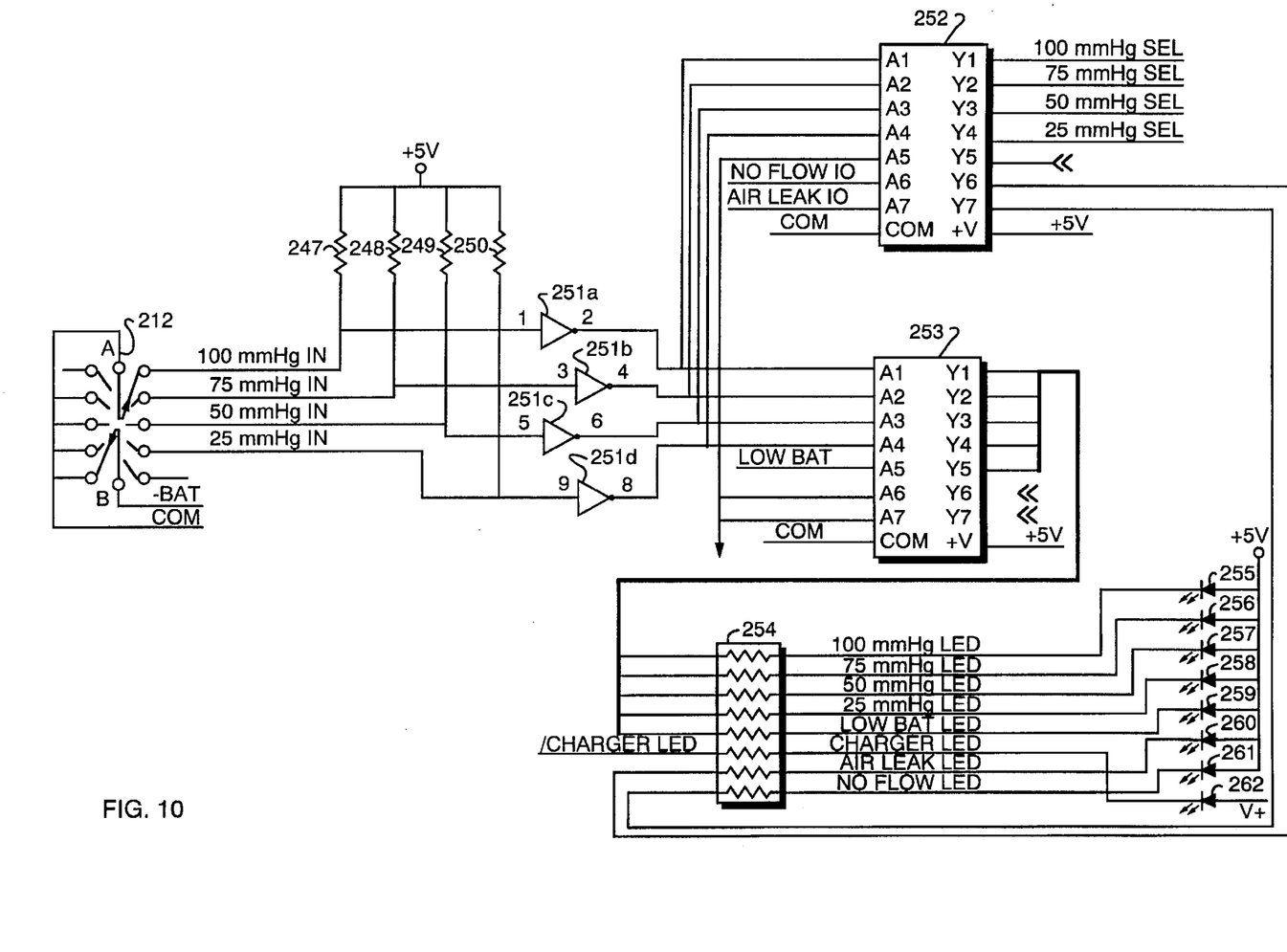
FIG. 10 is a schematic drawing of the selector switch and display circuitry.
Figure 11A:
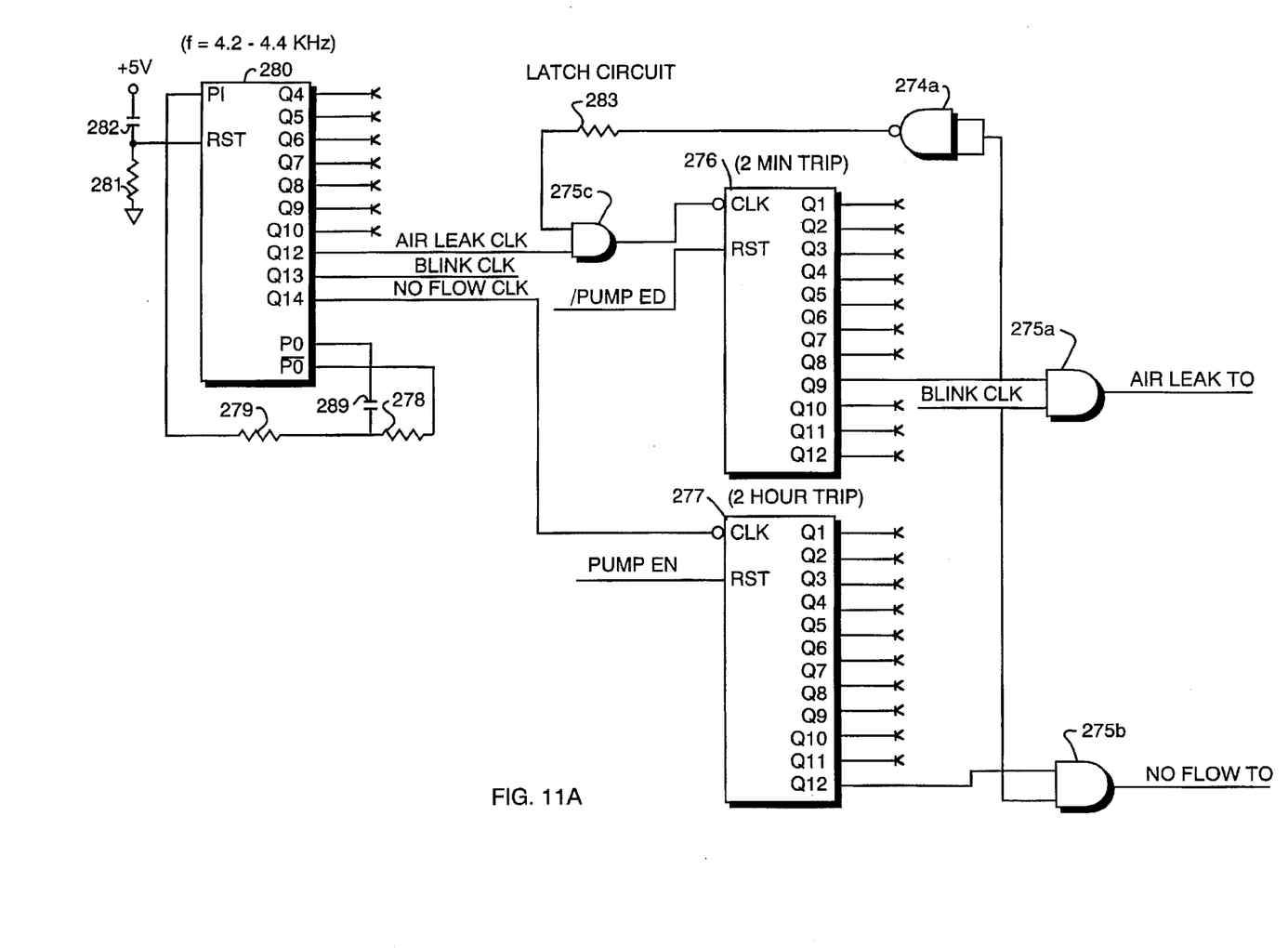
FIG. 11 is a schematic drawing of the vacuum pump control circuit.
Figure 11B:
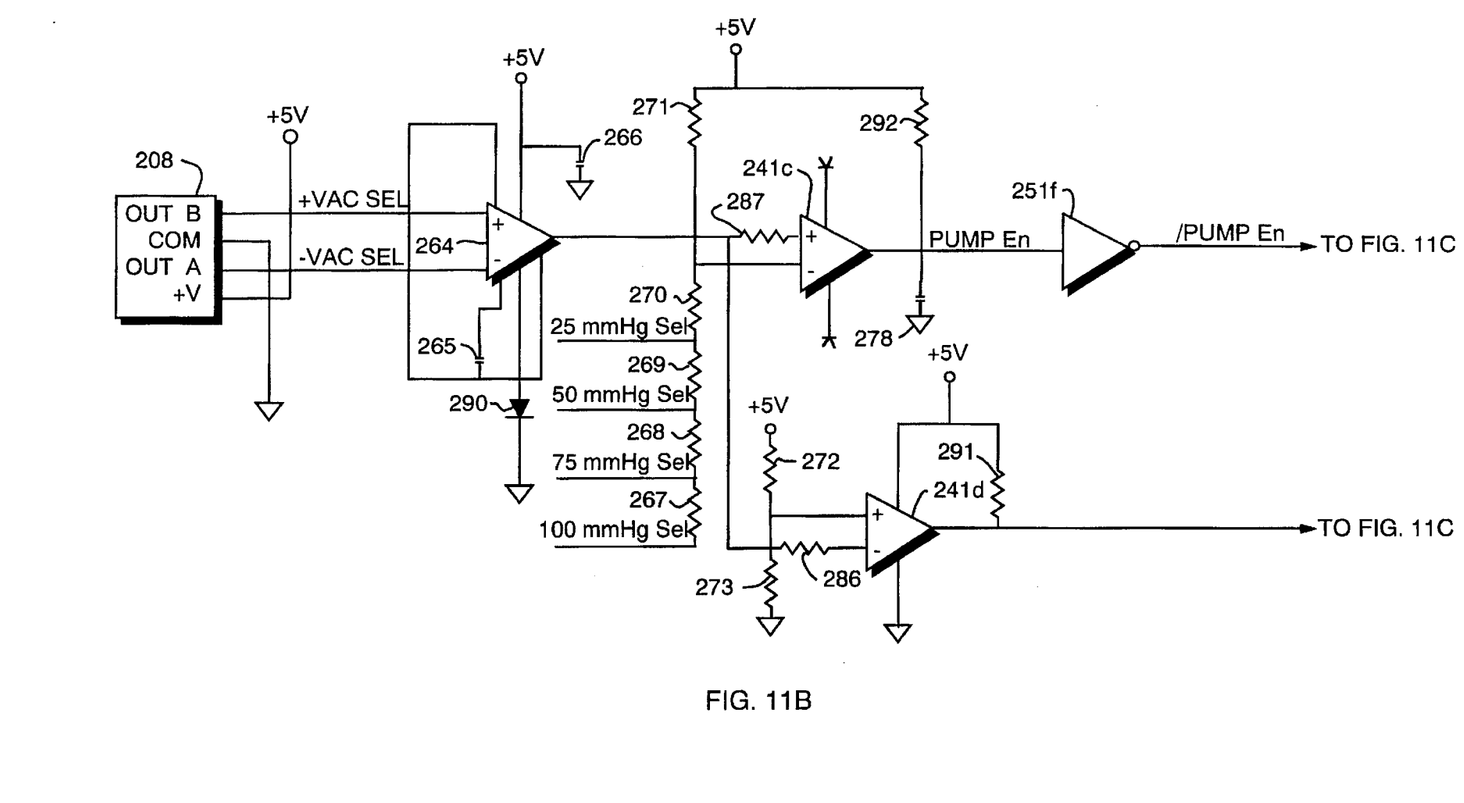
Figure 11C:
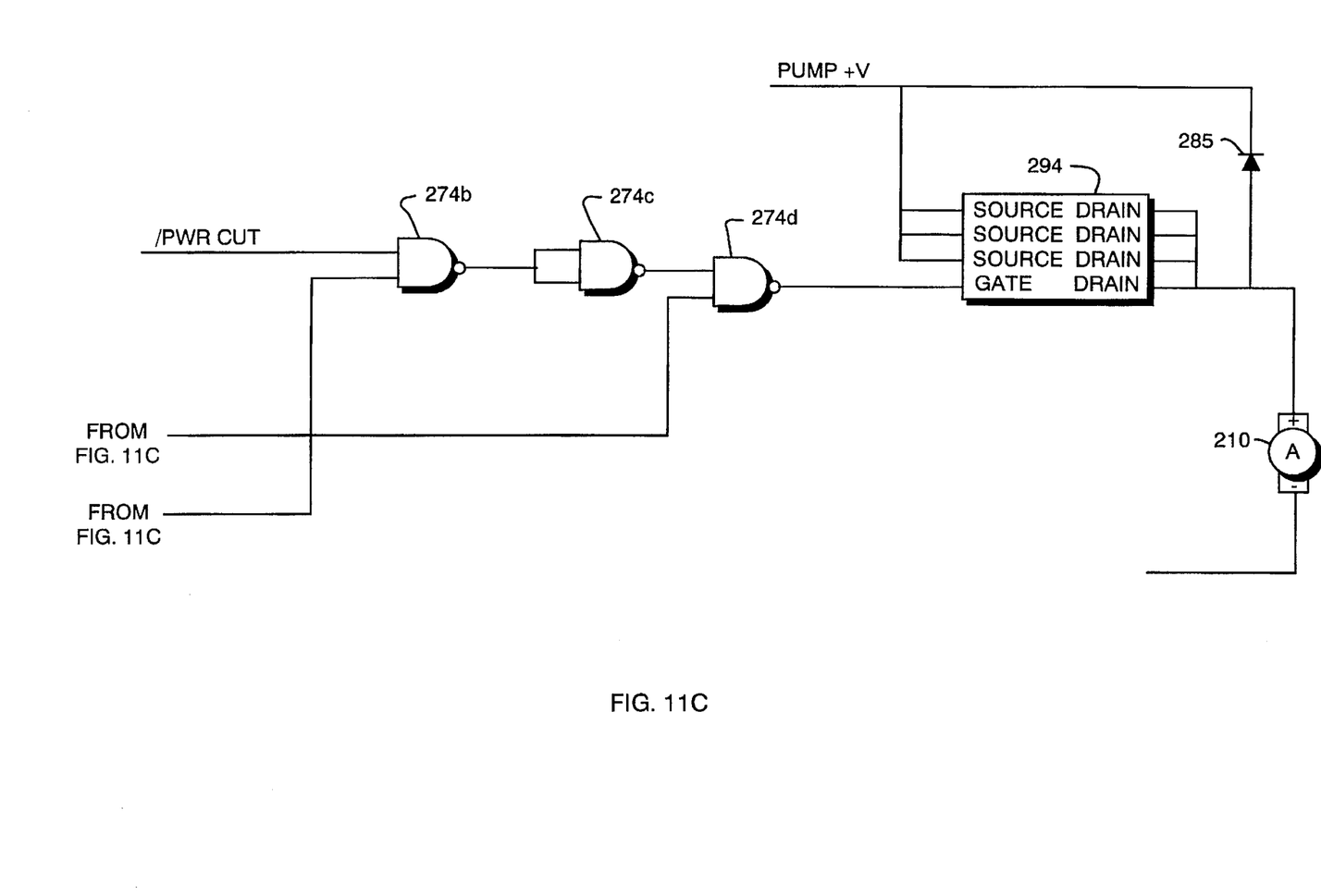

Turn now to FIGS. 10 and 11, which illustrate in greater detail selector switch 212, the display circuitry and the control logic. The varying levels of vacuum selection using switch 212 accommodate different types of tissue and drainage requirements. For example, muscle can withstand relatively high suction levels that might damage more delicate tissue. Selector switch 212 selectively grounds a terminal of one of the resistors 247–250. The input signal is then inverted by inverting buffers 251a–251d. The inverted output signal then is the input source signal to the current sink drivers 252, 253. These drivers serve as current sinks at the outputs Y1–4 in response to high logic signals at the corresponding inputs A1–4. Specifically, in response to a high voltage signal at one of inputs A1–A4, the first driver will serve as a current sink for one of outputs Y1–Y2 to generate a 100, 75, 50, and 25 mmHg select signal(mmHg Sel).

The first driver 252 also receives an air leak signal (Air leak TD) and a no flow signal (No Flow TD). In response to these signals, the corresponding light emitting diodes LED 260 and 261 are driven through a resistive current limiter 254. In a similar way, the second driver 253 drives LEDs 255–260 through the current limiter 254 in response to the outputs of one of the inverters 251a–251d (i.e., 100, 75, 50, and 25 mmHg selection signals, the low battery (Low Bat) signal indicating the low battery condition, and the charge indication signal (Charger LED).

With particular reference to the additional control logic shown in FIG. 11, a sensor analog differential amplifier 264 compares inputs (+VAC sen, –VAC sen) received from a piezoelectric bridge pressure detector 208 (see FIG. 8) which senses the pressure within the reservoir 12. Sensor amplifier 264 amplifies the voltage difference between the pressure detector inputs (+VAC sen, –VAC sen) by a fixed gain of 100.

A pump-enable comparator 241c generates a pump-enable signal in response to a comparison between a reference voltage indicative of the selected vacuum level received at its non-inverting input and the signal from the sensor amplifier 264, which is indicative of the vacuum pressure within the reservoir. A series of cascaded resistors 267–271 are connected to +5 V and serve as a selected voltage divider network. The 25, 50, 75, 100 mmHg select signals are then received at the junctions between each one of these resistors. As a result, depending upon which of these signals is active, the 5 V supply voltage is divided and serves as a reference voltage to the non-inverting input of comparator 241c. The resistances of resistors 267–271 and the gain of sensor amplifier 264 are selected such that comparator 241c generates an active pump-enable signal (Pump En) when the pressure within the reservoir 12 has fallen below the pressure selected by the selector switch 212. In other words, the resistors 267–271 are selected such that when the pressure in the reservoir 12 is the same or near the pressure indicated by the active one of the select signal, a voltage is presented to the non-inverting input that corresponds to the voltage produced by the sensor amplifier 208.

Preferably the design includes an over-pressure detector, which provides a level of redundancy to protect the patient. The over-pressure detector includes an over-pressure comparator 241d, which receives a divided voltage reference at its non-inverting input via a pair of resistors 272 and 273. This voltage corresponds to the voltage generated by the sensor amplifier 208 in response to a reservoir pressure of 110 mmHg. Should the sensed pressure reach this level, the over-pressure detector generates an active over-pressure signal (/Over_pres) that disables the vacuum source as discussed below. This circuit primarily protects against a damaged or broken vacuum selector switch or associated control circuitry failure.

A power MOSFET 284 electrically connects the PUMP+V line to the pump motor 210 in response to a system-enable signal, (/Sys_Enable), which is received at the gate of MOSFET 284. An active system-enable signal causes the MOSFET 284 to supply power to the pump motor 210. The system-enable signal can be active only when the /Over_pres signal and the /PWR_CUT signal and the pump-enable signals are high.

Two possible problems that may arise in the course of wound drainage can be detected by monitoring the operation of the pump motor 210. First, should pump motor 210 run continuously because the reservoir 12 fails to reach the selected level of vacuum, the likely cause is an air leak in the system. Leaks can result from damage to the disposable, improper installation or poor tubing Sealing around the wound. The second condition, should pump motor 210 fail to run at all or run only infrequently, an obstruction is probably blocking fluid flow into reservoir 12. Both of these malfunctions may be detected by a clock-timer circuit which measures the on/off time of pump motor 210. The clock timer circuit generates an initial fast air-leak clock signal (Air Leak CLK) and an initial slow noflow clock signal (No Flow CLK). A ripple counter 276 counts a two-minute interval from the air-leak clock signal (as long as the pump-enable signal is continually active). If the two minute counter counts out while the pump 210 is still running, the air-leak signal (Air Leak TD) is generated and latched by the circuit established by NAND gates 274a, 274c.

A two-hour ripple trip counter 277 counts the initial slow no-flow clock signal when the pump enable signal (Pump en) is inactive and, if it counts out, generates the no-flow signal (No Flow TD). This signal is not latched, however, since the length of time associated with the no-flow fault condition leaves ample time for a nurse or other operator to recognize the condition. With renewed reference to FIG. 10, the air-leak signal (Air leak TD) and the no-flow signal (No flow TD) trigger the driver 252 to operate the LEDs 260 and 261, respectively, to provide an indication to the operator of the air-leak or no-flow condition.

While this invention has been particularly shown and described with reference to preferred embodiments thereof, it will be understood by those skilled in the art that various changes in form and details may be made therein without departing from the spirit and scope of the invention as defined by the appended claims. For example, although the present invention has been described in the context of blood recovery and return, the invention can be used to recover or process any biological fluid. In addition, although selector valve 38 is depicted to be hand-operated, a solenoid or pneumatic valve can be employed instead. Furthermore, reservoir 12 can be coupled to a remotely located vacuum source by a suitable length of tubing.

What is claimed is:

1. Apparatus for collecting and salvaging blood, the apparatus comprising:
   a. a first chamber for collecting blood;
   b. an inlet port for admitting blood into the first chamber;
   c. a second chamber fluidly connected to the first chamber for receiving blood therefrom;
   d. a vacuum port associated with the first chamber for coupling the first chamber to a vacuum source; and
   e. a selector valve in fluid communication with the second chamber for alternatively venting the second chamber or coupling the second chamber to the vacuum port.

2. The apparatus of claim 1 wherein the first chamber is located above the second chamber.

3. The apparatus of claim 2 wherein the first and second chambers are fluidly connected by a drain valve capable of closing when the second chamber is vented while the first chamber is coupled to the vacuum source, the closing of the drain valve allowing the first chamber to remain under a vacuum.

4. The apparatus of claim 3 wherein the drain valve is pressure-operated, the drain valve closing when subjected to a pressure differential between the first and second chambers.

5. The apparatus of claim 1 further comprising a filter for filtering particles from blood entering the first chamber.

6. The apparatus of claim 3 further comprising a lipid separator in the first chamber for separating lipids from the blood.

7. The apparatus of claim 6 wherein the lipid separator comprises a lipid filter for filtering lipids from the blood.

8. The apparatus of claim 6 wherein the lipid separator comprises:
   a. a partition within the first chamber for defining separate portions thereof, the partition having an opening at its lower end that permits blood to pass therethrough; and
   b. a dam spaced between the partition and the drain valve such that when blood flowing under the partition reaches the height of the dam, the blood flows over the dam and into the drain valve,
   c. the dam and the partition thereby cooperating to prevent passage of buoyant material into the drain valve.

9. The apparatus of claim 1 further comprising a transfusion bag in fluid communication with the second chamber for receiving blood therefrom.

10. The apparatus of claim 1 further comprising:
    a. an infusion port for infusing fluid into the first chamber; and
    b. an auxiliary port for admitting fluid into the first chamber.

* * * * *